US00PP35538P2

(12) United States Plant Patent
van Sambeek

(10) Patent No.: US PP35,538 P2
(45) Date of Patent: Dec. 12, 2023

(54) ***LEUCANTHEMUM* PLANT NAMED 'DOLEUSWEDAIZA'**

(50) Latin Name: ***Leucanthemum* x *superbum* X *Leucanthemum maximum***
Varietal Denomination: Doleuswedaiza

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/119,699

(22) Filed: Mar. 9, 2023

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Leucanthemum* plant named 'Doleuswedaiza', characterized by its upright and mounded plant habit; freely branching habit; strong and upright flowering stems; early and freely flowering habit; semi-double type inflorescences with light yellow-colored ray florets and dark yellow-colored disc florets; good inflorescence longevity; and good garden performance.

2 Drawing Sheets

Figure 1:
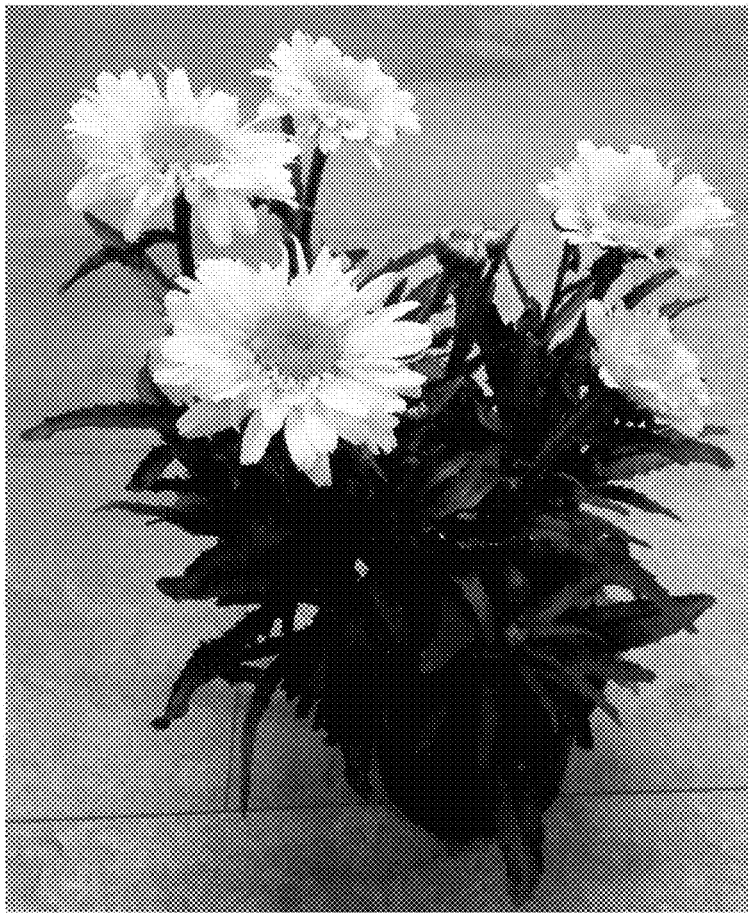

Botanical designation: *Leucanthemum* x *superbum* X *Leucanthemum maximum.*
Cultivar denomination: 'DOLEUSWEDAIZA'.

CROSS-RESTATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 15, 2022, application number 2022/1926. Foreign priority is not claimed to this application.

BACKGROUND OF THE INVENTION

The present invention relates to a new and distinct cultivar of *Leucanthemum* plant, botanically known as *Leucanthemum* x *superbum* X *Leucanthemum maximum* and hereinafter referred to by the name 'Doleuswedaiza'.

The new *Leucanthemum* plant is a product of a planned breeding program conducted by the Inventor in Aalsmeer, The Netherlands. The objective of the breeding program is to create new compact *Leucanthemum* plants with numerous unique and attractive inflorescences.

The new *Leucanthemum* plant originated from a cross-pollination made by the Inventor in June, 2014 of *Leucanthemum* x *superbum* 'Goldfinch', disclosed in U.S. Plant Pat. No. 24,499, as the female, or seed, parent with a proprietary selection of *Leucanthemum maximum* identified as code number LC-003, not patented, as the male, or pollen, parent. The new *Leucanthemum* plant was discovered and selected by the Inventor as a single flowering plant from within the progeny of the stated open-pollination in a controlled environment in Aalsmeer, The Netherlands in April, 2015.

Asexual reproduction of the new *Leucanthemum* plant by vegetative terminal cuttings in Aalsmeer, The Netherlands, since May, 2015 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doleuswedaiza'. These characteristics in combination distinguish 'Doleuswedaiza' as anew and distinct *Leucanthemum* plant:

1. Upright and mounded plant habit.
2. Freely branching habit.
3. Strong and upright flowering stems.
4. Early and freely flowering habit.
5. Semi-double type inflorescences with light yellow-colored ray florets and dark yellow-colored disc florets.
6. Good inflorescence longevity.
7. Good garden performance.

Plants of the new *Leucanthemum* differ primarily from plants of the female parent, 'Goldfinch' in growth habit as plants of the new *Leucanthemum* grow faster than plants of 'Goldfinch'.

Plants of the new *Leucanthemum* differ primarily from plants of the male parent selection in inflorescence type and ray floret color as plants of the new *Leucanthemum* have semi-double type inflorescences with light yellow-colored ray florets whereas plants of the male parent selection have single-type inflorescences with white-colored ray florets.

Plants of the new *Leucanthemum* can be compared to plants of *Leucanthemum superbum* 'Real Neat', disclosed in U.S. Plant Pat. No. 26,185. In side-by-side comparisons, plants of the new *Leucanthemum* differ from plants of 'Real Neat' in the following characteristics:

1. Plants of the new *Leucanthemum* flower later than plants of 'Real Neat'.
2. Plants of the new *Leucanthemum* have semi-double type inflorescences whereas plants of 'Real Neat' have spider-type inflorescences.
3. Ray florets of plants of the new *Leucanthemum* are light yellow in color whereas ray florets of plants of 'Real Neat' are white in color.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph on the first sheet (FIG. 1) is a side perspective view of a typical flowering plant of 'Doleuswedaiza' grown in a container.

Figure 2:
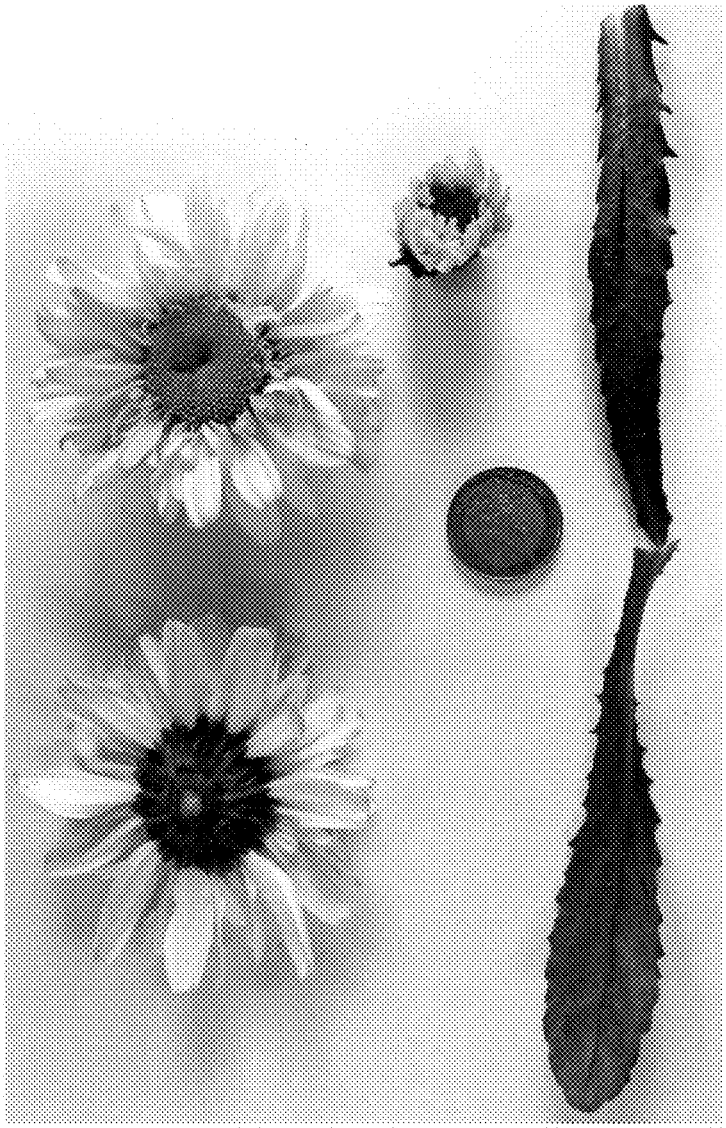

The photograph on the second sheet (FIG. 2) comprises close-up views of a typical inflorescence bud and the upper and lower surfaces of typical inflorescences and leaves of plants of 'Doleuswedaiza'.

DETAILED BOTANICAL DESCRIPTION

The aforementioned photographs and following observations and measurements describe plants grown in 13-cm containers in Aalsmeer, The Netherlands during the early summer initially in a greenhouse and finished in an outdoor nursery and grown under conditions and cultural practices which approximate those generally used in commercial *Leucanthemum* plant production. During the production of the plants, day temperatures averaged 21C and night temperatures averaged 15C. Plants were 16 weeks old when the photographs and description were taken. In the following description, color references are made to The Royal Horticultural Society Colour Chart, Fifth Edition, except where general terms of ordinary dictionary significance are used. Measurements represent averages for typical flowering plants.

Botanical classification: *Leucanthemum* x *superbum* X *Leucanthemum maximum* 'Doleuswedaiza'.

Parentage:

*Female, or seed, parent.*—*Leucanthemum* x *superbum* 'Goldfinch', disclosed in U.S. Plant Pat. No. 24,499.

*Male, or pollen, parent.*—Proprietary selection of *Leucanthemum maximum* identified as code number LC-003, not patented.

Propagation:

*Type.*—Terminal vegetative cuttings.

*Time to initiate roots, summer.*—About twelve days at temperatures about 26C.

*Time to initiate roots, winter.*—About two weeks at temperatures about 23C.

*Time to produce a rooted young plant, summer.*—About two weeks at temperatures about 23C.

*Time to produce a rooted young plant, winter.*—About 16 days at temperatures about 18C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Moderately freely branching, medium density.

Plant description:

*Plant and growth habit.*—Herbaceous perennial; upright and mounded plant habit; moderately vigorous growth habit; freely branching habit with about eight primary branches developing per plant.

*Plant height.*—About 26 cm.

*Plant width.*—About 31 cm.

*Branch description.*—Length: About 25 cm. Diameter: About 7 mm. Internode length: About 3.5 cm. Strength: Strong. Aspect: Erect to about 40 degrees from vertical. Texture and luster: Pubescent; glossy. Color, developing: Close to 146B. Color, developed: Close to N137A.

*Leaf description.*—Arrangement: Alternate; simple; sessile. Length: About 10.5 cm. Width: About 2.3 cm. Shape: Lanceolate. Apex: Acute. Base: Truncate. Margin: Serrate with shallow and divergent indentations; undulate. Texture and luster, upper and lower surfaces: Smooth, glabrous; glossy. Venation pattern: Pinnate. Color: Developing leaves, upper surface: Close to N137C. Developing leaves, lower surface: Close to 137B. Fully developed leaves, upper surface: Close to N137A; venation, close to 137B. Fully developed leaves, lower surface: Close to N137A; venation, close to 137C.

Inflorescence description:

*Appearance.*—Semi-double type inflorescences with ligulate-shaped ray florets and tubular disc florets; inflorescences held upright on strong peduncles, inflorescences face mostly upright; ray and disc florets develop acropetally on a capitulum.

*Fragrance.*—Slightly fragrant, pleasant.

*Flowering response.*—Plants begin flowering about twelve weeks after planting; plants flower naturally during June and July in The Netherlands.

*Postproduction longevity.*—Inflorescences maintain good substance for about six to eight weeks on the plant; inflorescences persistent.

*Quantity of inflorescences.*—Freely flowering habit, about 22 inflorescences develop per plant during the flowering season.

*Inflorescence size.*—Diameter: About 8 cm. Depth (height): About 3 cm. Disc diameter: About 2.5 cm.

*Receptacles.*—Height: About 3 mm. Diameter: About 1.9 cm. Color: Close to 145B.

*Inflorescence buds.*—Height: About 1.4 cm. Diameter: About 1.8 cm. Shape: Flattened sphere. Texture and luster: Smooth, glabrous; glossy. Color: Close to 2B.

*Ray florets.*—Quantity per inflorescence: About 80 arranged in about three to four whorls. Length: About 3.3 cm. Width: About 1.1 cm. Shape: Ligulate. Apex: Emarginate. Base: Attenuate and fused at the base. Margin: Entire; slightly undulate. Aspect: Mostly horizontal to slightly reflexing with development. Texture and luster, upper and lower surfaces: Smooth, glabrous; matte. Color: When opening, upper and lower surfaces: Close to 2B. Fully opened, upper surface: Close to 3D; color does not change with subsequent development. Fully opened, lower surface: Close to 2D; color does not change with subsequent development.

*Disc florets.*—Quantity per inflorescence: About 476 massed at the center of the receptacle arranged in about 14 whorls. Length: About 6 mm. Diameter: About 1 mm. Shape: Fused tubular. Apex: Acute, five-pointed. Texture and luster, inner and outer surfaces: Smooth, glabrous; matte. Color: When opening, inner and outer surfaces: Close to 15A. Fully opened, inner and outer surfaces: Close to 15B; color does not change with subsequent development.

*Involucral bracts.*—Quantity per inflorescence: About 80 arranged in about three or four whorls. Length: About 9 mm. Width: About 5 mm. Shape: Deltoid. Apex: Acute. Base: Truncate. Margin: Entire. Texture and luster, upper surface: Smooth, glabrous; semi-glossy. Texture and luster, lower surface: Smooth, glabrous; glossy. Color, upper and lower surfaces: Close to 137A.

*Peduncles.*—Length: About 3.5 cm to 5 cm. Diameter: About 6 mm. Strength: Strong. Aspect: Erect to about 10 degrees from vertical. Texture and luster: Pubescent; glossy. Color: Close to 137A.

*Reproductive organs.*—Androecium: Present on disc florets only. Quantity per floret: Five per disc floret. Filament length: About 2 mm. Filament color: Close to 144C. Anther shape: Roughly rectangular. Anther size: About 1 mm by 3 mm. Anther color: Close to 17A. Pollen amount: Abundant. Pollen color: Close to 17A. Gynoecium: Present on ray and disc florets. Quantity per floret: One. Pistil length: About 6 mm. Stigma diameter: About 1 mm. Stigma shape: Biparted. Stigma color: Close to 153A. Style length: About 4 mm. Style color: Close to 144C. Ovary color: Close to 142C.

*Seeds and fruits.*—To date, seed and fruit development have not been observed on plants of the new *Leucanthemum.*

Pathogen & pest resistance: To date, plants of the new *Leucanthemum* have not been observed to be resistant to pathogens and pests common to *Leucanthemum* plants.

Garden performance: Plants of the new *Leucanthemum* have exhibited good tolerance to rain, wind and to tolerate temperatures ranging from −30C to about 35C and to be suitable for USDA Hardiness Zones 4 through 9.

It is claimed:

1. A new and distinct *Leucanthemum* plant named 'Doleuswedaiza' as illustrated and described.

* * * * *